(12) United States Patent
Vavelin et al.

(10) Patent No.: US 11,865,348 B2
(45) Date of Patent: *Jan. 9, 2024

(54) IMPLANTABLE MEDICAL DEVICE SYSTEM WITH MULTI-BAND ANTENNA ARRANGEMENT

(71) Applicant: Cochlear Limited, Macquarie University (AU)

(72) Inventors: Guilhem Yvan Vavelin, Nice (FR); Thomas Leroux, Valbonne (FR); Gauthier Jodin, Antibes (FR)

(73) Assignee: Cochlear Limited, Macquarie University (AU)

( * ) Notice: Subject to any disclaimer, the term of this patent is extended or adjusted under 35 U.S.C. 154(b) by 387 days.

This patent is subject to a terminal disclaimer.

(21) Appl. No.: 17/273,170

(22) PCT Filed: Nov. 27, 2019

(86) PCT No.: PCT/IB2019/060243
§ 371 (c)(1),
(2) Date: Mar. 3, 2021

(87) PCT Pub. No.: WO2020/115615
PCT Pub. Date: Jun. 11, 2020

(65) Prior Publication Data
US 2021/0351508 A1 Nov. 11, 2021

Related U.S. Application Data

(60) Provisional application No. 62/774,367, filed on Dec. 3, 2018.

(51) Int. Cl.
*A61N 1/37* (2006.01)
*A61N 1/372* (2006.01)
(Continued)

(52) U.S. Cl.
CPC ..... *A61N 1/37229* (2013.01); *A61N 1/36038* (2017.08); *H01Q 1/273* (2013.01);
(Continued)

(58) Field of Classification Search
CPC .. A61N 1/37229; A61N 1/36038; H01Q 5/30; H01Q 1/273; H04B 5/005; H04B 5/0081; H04R 25/55
See application file for complete search history.

(56) References Cited

U.S. PATENT DOCUMENTS 5,630,835 A * 5/1997 Brownlee .......... A61N 1/37229
128/903
7,260,435 B2 8/2007 Ibrahim
(Continued)

FOREIGN PATENT DOCUMENTS

KR 10-2014-0099209 A 8/2014

OTHER PUBLICATIONS

International Search Report and Written Opinion in counterpart International Application No. PCT/IB2019/060243, dated Mar. 19, 2020, 8 pages.

*Primary Examiner* — Junpeng Chen
(74) *Attorney, Agent, or Firm* — Edell, Shapiro & Finnan, LLC

(57) ABSTRACT

Embodiments presented herein are generally directed to techniques that provide a medical device component with the ability to communicate in both the near-field and far-field via a single antenna arrangement. More specifically, a medical device component includes an electronics circuit, a coil driver, an antenna arrangement, and an isolation circuit. The isolation circuit operates to extract far-field signals received at the antenna arrangement and provide these signals to the (Continued)

electronics circuit. The electronics circuit is protected from near-field signals received at the antenna arrangement via the isolation circuit.

20 Claims, 8 Drawing Sheets

(51) Int. Cl.
*H01Q 5/30* (2015.01)
*H01Q 1/27* (2006.01)
*H04B 5/00* (2006.01)
*A61N 1/36* (2006.01)
*H04R 25/00* (2006.01)

(52) U.S. Cl.
CPC .............. *H01Q 5/30* (2015.01); *H04B 5/005* (2013.01); *H04B 5/0081* (2013.01); *H04R 25/55* (2013.01)

(56) References Cited

U.S. PATENT DOCUMENTS

| | | | |
|---|---|---|---|
| 8,126,563 | B2 | 2/2012 | Ibrahim |
| 10,193,597 | B1* | 1/2019 | Garrido Lopez ........ H04B 1/38 |
| 2002/0123776 | A1* | 9/2002 | Von Arx ............ A61N 1/37223 607/60 |
| 2003/0114897 | A1* | 6/2003 | Von Arx ............ A61N 1/37276 607/60 |
| 2013/0018440 | A1 | 1/2013 | Chow et al. |
| 2013/0253612 | A1* | 9/2013 | Chow .................. A61N 1/3787 607/60 |
| 2014/0257432 | A1 | 9/2014 | Tahmasian et al. |
| 2016/0374124 | A1 | 12/2016 | Gothe et al. |
| 2018/0132745 | A1 | 5/2018 | Himmrich |
| 2019/0074585 | A1* | 3/2019 | Vavelin ............. A61N 1/37229 |

\* cited by examiner

US 11,865,348 B2

IMPLANTABLE MEDICAL DEVICE SYSTEM WITH MULTI-BAND ANTENNA ARRANGEMENT

BACKGROUND

Field of the Invention

The present invention relates generally to implantable medical device systems.

Related Art

Medical device systems having one or more implantable components, generally referred to herein as implantable medical device systems, have provided a wide range of therapeutic benefits to recipients over recent decades. In particular, partially or fully-implantable medical device systems such as hearing prosthesis systems (e.g., systems that include bone conduction devices, mechanical stimulators, cochlear implants, etc.), implantable pacemakers, defibrillators, functional electrical stimulation systems, etc., have been successful in performing lifesaving and/or lifestyle enhancement functions for a number of years.

The types of implantable medical device systems and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device system.

SUMMARY

In one aspect an external component of an implantable medical device system is provided. The external component comprises: a multi-band antenna arrangement; an electronics circuit; a coil driver coupled between the multi-band antenna arrangement and the electronics circuit and configured to receive, via the multi-band antenna arrangement, near-field signals from an implantable component inductively coupled to the multi-band antenna arrangement; and an isolation circuit coupled between the multi-band antenna arrangement and the electronics circuit and configured to receive, via the multi-band antenna arrangement, far-field signals from at least one external and to provide the far-field signals to the electronics circuit.

In another aspect a medical device component is provided. The medical device component comprises: an electronics circuit, including far-field wireless circuitry; an antenna arrangement configured to receive both near-field radio-frequency (RF) signals and far-field RF signals from one or more other devices positioned; a coil driver disposed between the electronics circuit and the antenna arrangement and configured to provide the near-field RF signals to the electronics circuit; an isolation coupler disposed between the electronics circuit and the antenna arrangement and configured to provide the far-field RF signals to the electronics circuit; and first and second capacitors connected in series with a primary side of the isolation coupler, and wherein the first and second capacitors are disposed on opposing sides of the primary side of the isolation coupler.

In another aspect a method is provided. The method comprises: receiving, at an antenna arrangement of a medical device component, near-field radio-frequency (RF) signals; receiving, at the antenna arrangement of the medical device component, far-field RF signals; providing the far-field RF signals to an electronics circuit via a coil driver; and providing only the near-field signals to the electronics circuit via an isolation circuit.

BRIEF DESCRIPTION OF THE DRAWINGS

Embodiments of the present invention are described herein in conjunction with the accompanying drawings, in which.

DETAILED DESCRIPTION

Figure 1:
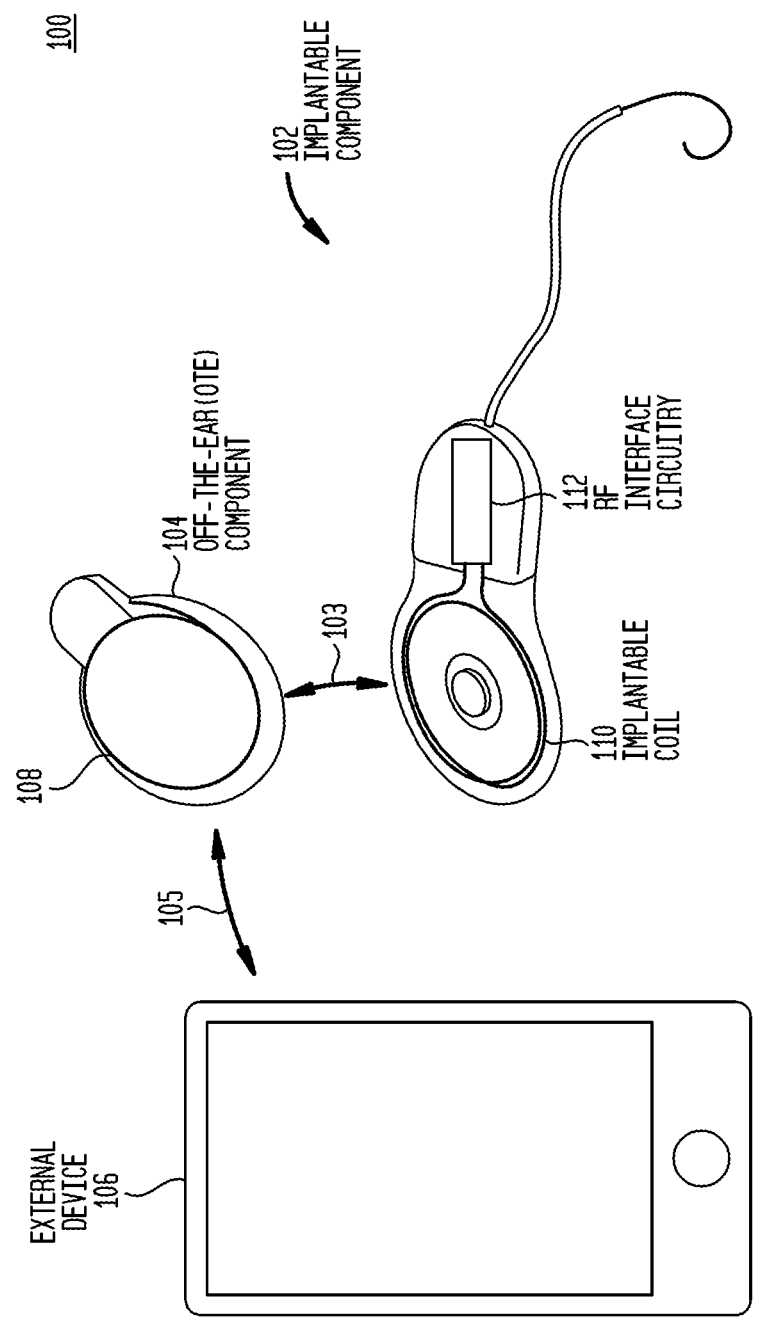
FIG. 1 is a block diagram illustrating a cochlear implant system, in accordance with certain embodiments presented herein.

Implantable medical device systems include one or more components that are temporarily or permanently implanted within the body of a recipient. It is common for implantable medical device systems to also include, or operate in conjunction with, one or more external components/devices. In general, an external component provides functionality (e.g., processing capabilities, battery charging, etc.) that ensures proper operation of the associated implantable component(s). As a result, the external component transcutaneously communicates with (e.g., wirelessly transmits data to, wirelessly receives data from, and/or wirelessly provides power to) an associated implantable component. In certain arrangements, the external component of an implantable medical device system may also wirelessly communicate with other external devices.

In general, the electromagnetic field surrounding a transmitting antenna can be broken into a near-field region/portion (the near-field) and a far-field region (the far-field). The boundary between the two regions is only generally defined and it depends on the dominant wavelength ($\lambda$) emitted by the antenna. The near-field and the far-field have different energies. The near-field is primarily magnetic in nature and is based on inductive coupling, while the far-field has both electric and magnetic components (i.e., electromagnetic field/radiation). Therefore, as used herein, near-field communication refers to short-range wireless connectivity that uses magnetic field induction (inductive coupling) to enable power and/or data communication between devices that are in close proximity to one another. In contrast, far-field communication refers to long-range wireless connectivity in the electromagnetic field region dominated by electromagnetic fields with electric dipole characteristics.

In practice, near-field and the far-field signals are sent at different frequencies, where lower frequencies are typically used in the near-field and higher frequencies are used in the far-field. For example, the near-field signals may be transmitted at approximately 5 Megahertz (MHz), at approximately 6.78 MHz, at approximately 13.56 MHz, at approximately 27.12 MHz, etc. The far-field signals may be transmitted at frequencies, above 15 MHz, more preferably well above 50 MHz (e.g., on the order of a few Gigahertz (GHz)). For example, far-field signals may be signals in the very high frequency (VHF) range, signals in the ultra-high frequency (UHF) range, or a higher frequency range.

Since the external and implantable components of an implantable medical device system are located within close proximity to one another, the transcutaneous wireless communication there between typically occurs in the near-field. Conversely, an external component of an implantable medical device system may not be located in such close proximity to other external devices. Accordingly, the wireless communication between the external component and other external devices typically occurs in the far-field. Therefore, in order for the external component to wirelessly communicate with both the implantable component and other external devices, there is a need for the external component to operate in both the near-field and the far-field and, accordingly, at different wireless frequencies. In conventional arrangements, this requirement for operation at in both the near-field and the far-field also requires the external component to include two separate and distinct wireless communication paths, including two physically separate transmitting/receiving antennas (e.g., two separate coils, where one coil is used for the near-field communication and the other coil is used for the far-field communication).

Increasingly, there is a desire to make medical device components, such as external components of implantable medical device systems, as small as possible (e.g., for aesthetic reasons, safety reasons, etc.). However, the need for two physically separate transmitting/receiving antennas, as detailed above, inherently limits how small a medical device component can be made. Presented herein are techniques that provide a medical device component with the ability to communicate in both the near-field and far-field, without the requirement for two separate and distinct wireless communication paths and, accordingly, without requiring two physically separate transmitting/receiving antennas.

More specifically, a medical device component in accordance with certain embodiments presented herein includes a coil driver and a near-field transmitting/receiving antenna arrangement that is used for communication in the near-field (e.g., transcutaneous wireless communication with an implantable component). The medical device component also comprises an electronics circuit, which includes far-field wireless circuitry that is coupled to the near-field transmitting/receiving antenna arrangement via an isolation circuit. The isolation circuit enables the far-field wireless circuitry to communicate with external devices in the far-field via the same transmitting/receiving antenna arrangement that is used for communication in the near-field. For example, the isolation circuit may comprise a high-pass filter and isolation coupler that operate to extract far-field signals received at the transmitting/receiving antenna arrangement and provide these signals to the far-field wireless circuitry. The field wireless circuitry is protected from near-field signals received at the at least one transmitting/receiving antenna arrangement via the high-pass filter and isolation coupler.

There are a number of different types of implantable medical device systems in which embodiments presented herein may be implemented. However, merely for ease of illustration, the techniques presented herein are primarily described with reference to one type of implantable medical device system, namely a cochlear implant system. It is to be appreciated that the techniques presented herein may be used in any other partially or fully implantable medical device system now known or later developed, including other auditory prosthesis systems, such as systems that include auditory brainstem stimulators, electro-acoustic hearing prostheses, middle ear prostheses, direct cochlear stimulators, bimodal hearing prostheses, etc. and/or other types of medical device systems, such as visual prosthesis systems, pain relief implants, pacemakers, etc.

FIG. 1 is block diagram of an exemplary cochlear implant system 100 in which embodiments presented herein are implemented. The cochlear implant system 100 comprises an implantable component 102 configured to be implanted under the skin/tissue of a recipient, an external component 104 and a second or auxiliary external device 106.

In the example of FIG. 1, the external component 104 is an external device in the shape of a button configured to be worn "off-the-ear" of a recipient. As such, the specific external component 104 is also sometimes referred to as an off-the-ear (OTE) component or button. The external device 106 is, in this example, a mobile phone. However, the external device 106 could alternatively be a remote control unit, a fitting system, or any other computing device configured for far-field communication.

As shown in FIG. 1, the OTE component 104 is configured to wirelessly communicate with both the implantable component 102 and the external device 106. That is, the OTE component 104 is configured for near-field wireless communication with the implantable component 102, and for far-field wireless communication with the external device 106. In FIG. 1, the near-field wireless communication between OTE component 104 and implantable component 102, sometimes referred to herein as a "near-field wireless link," is represented by arrow 103. Similarly, the far-field wireless communication between OTE component 104 and external device 106, sometimes referred to herein as a "far field wireless link," is represented by arrow 105. As described further below, the OTE component 104 comprises a single transmitting/receiving arrangement that is used for both the near-field and the far-field wireless communication. Shown in FIG. 1 is a primary inductive coil (primary coil) 108, which forms part of the transmitting/receiving arrangement used for both the near-field and the far-field communication.

As shown in FIG. 1, the implantable component 102 comprises, among other elements, an implantable inductive coil (implantable coil) 110 and radio-frequency (RF) circuitry 112. The implantable coil 110 and RF circuitry 112 enable the implantable component 102 to wirelessly communicate with OTE component 104 via the near-field wireless link 103 (i.e., the near-field wireless link 103 is formed between primary coil 108 and implantable coil 110). It is to be appreciated that implantable component 102 would include other components, such as a stimulator unit, electrode assembly, etc., that, for ease of illustration, have been omitted from FIG. 1.

Figure 2:
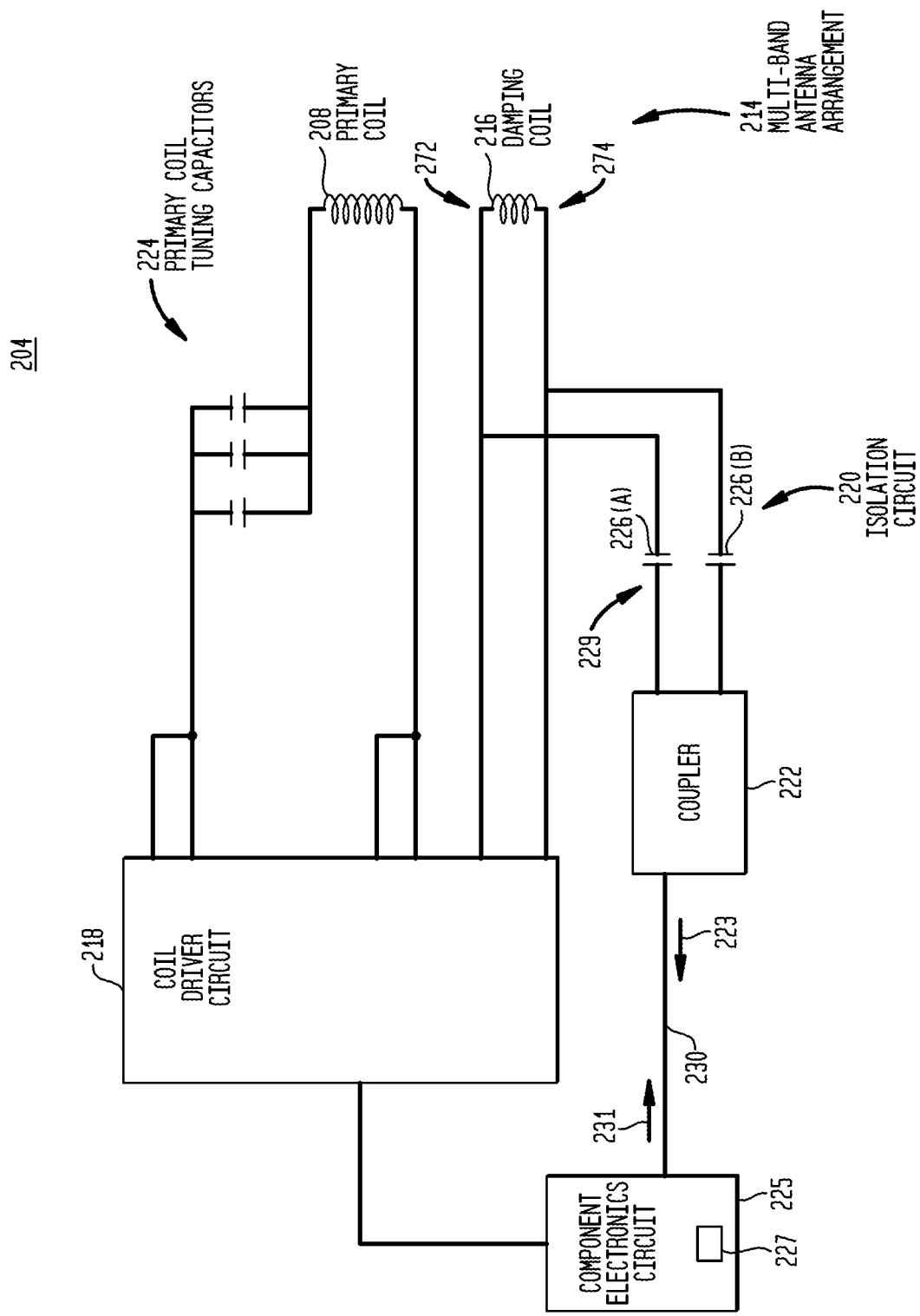
FIG. 2 is a simplified schematic diagram illustrating a medical device component, in accordance with certain embodiments presented herein.

FIG. 2 is a simplified schematic diagram illustrating further details of an example external component, such as OTE component 104, that is configured in accordance with certain embodiments presented herein. For ease of description, the external component of FIG. 2 is referred to as external component 204.

External component 204 comprises a single transmitting/receiving antenna arrangement 214, sometimes referred to as a "multi-band antenna arrangement." In the example of FIG. 2, the multi-band antenna arrangement 214 comprises a primary coil 208 and a damping coil 216. The external component 204 also comprises, among other elements, a coil driver circuit 218, one or more primary coil tuning capacitors 224, an isolation circuit 220, and a component electronics circuit 225.

As shown, in FIG. 2 the isolation circuit 220 comprises an isolation coupler 222 and two capacitors 226(A) and 226(B), which form a high-pass filter with at least one input of the coupler. Each of the coil driver circuit 218 and the isolation coupler 222 have electrical connections to the component electronics circuit 225. The component electronics circuit 225 may comprise, among other elements, processors, memory, far-field wireless circuitry 227, etc. For ease of illustration, FIG. 2 only shows the far-field wireless circuitry 227 within the component electronics circuit 225.

In operation, the primary coil 208 is used for near-field communication with an implantable component (e.g., implantable component 102 of FIG. 1). That is, in order to transmit near-field signals to an implantable component, the coil driver circuit 218 drives the primary coil 208 with current signals which generates a modulated magnetic field which is measured by the implantable coil in the implantable component (i.e., via induced current flow in the implantable coil). When receiving near-field signals, the implantable coil (e.g., coil 110 in FIG. 1) within the implantable component similarly generates a modulated magnetic field, which induces a flow of current signals in the primary coil 208. The current signals received by (induced in) the primary coil 208 are provided to the coil driver circuit 218 and further processed for subsequent use by the external component 216 at component electronics circuit 225.

As previously noted, the near-field communication may occur in a particular frequency range/band. The primary coil tuning capacitors 224 may be used to control or dictate the near-field communication frequency. Moreover, during near-field communication, the damping coil 216 is used to optimize the integrity of the near-field communication link over a large range of recipient skin flap thicknesses. The damping coil 216 is not, but instead is used to lower the "Q" (quality factor) during data transfer over the near-field communication link.

As noted, in addition to near-field communication, external components in accordance with embodiments presented herein, such as external component 204, are also configured for far-field communication. In the embodiment of FIG. 2, the external component 204 also uses the multi-band antenna arrangement 214 for this far-field communication. That is, the same antenna arrangement 214 is used for both near-field communication with an implantable component and for far-field communication with other external devices.

In FIG. 2, the dual-use of the multi-band antenna arrangement 214 for both near-field and far-field communication is enabled by the isolation circuit 220. That is, the isolation circuit 220 is configured such that the multi-band antenna arrangement 214 may be used to transmit or receive both near-field signals and far-field signals, potentially at the same time.

As noted, the isolation circuit 220 comprises an isolation coupler 222 and two capacitors 226(A) and 226(B) plus other potential matching components which have been omitted to ease illustration. In the example of FIG. 2, the isolation coupler 222 is connected to a first terminal 272 of the dampening coil 216 via the first capacitor 226(A) and to a second terminal 274 of the dampening coil 216 via the second capacitor 226(B) (i.e., capacitors 226(A) and 226(B) are connected between the isolation coupler 222 and the multi-band antenna arrangement 214). The capacitors 226(A) and 226(B), along with an inductance an input of the coupler 222, form a high-pass filter 229 for signals received at the multi-band antenna arrangement 214.

The isolation coupler 222 may be implemented in a number of different manners, but generally includes a first (primary) side (not shown in FIG. 2) that closes the antenna loop and a second (secondary) side (also not shown in FIG. 2) that is electrically isolated from the first side. The second side of the isolation coupler 222 generates a far-field output 223 that is provided to the component electronics circuit 225 through connection 230 (which may include potential matching components which have been omitted to ease illustration), while also electrically isolating the component electronics circuit 225, and far-field wireless circuitry 227, from direct current (DC) at the primary side connected to the multi-band antenna arrangement 214.

Due to the physical arrangement of the multi-band antenna arrangement 214, the multi-band antenna arrangement is exposed to both the near-field and far-field signals. However, as noted above, in the embodiment of FIG. 2 the capacitors 226(A) and 226(B), and the inductance of the primary side of the coupler 222, operate as a high-pass filter 229 that blocks the lower-frequency near-field signals. In other words, the isolation circuit 220 operates to extract a portion of the signals present at multi-band antenna arrangement 214, without exposing the component electronics circuit 225, and particularly the far-field wireless circuitry 227, to damage resulting from the receipt of the near-field signals at the same antenna arrangement. In addition, local ground is not required at the first side of the isolation coupler 222.

In terms of transmission, the primary coil 208 can be driven directly at the near-field tuned frequency (as a result of the serial tuning capacitors 224). In case of the damping coil 216, no current is sent there through, but the damped near-field signals are routed to ground. In both situations, the near-field signals are in a much lower frequency range than the far-field frequencies, and this discrimination is a result of the high-pass filter 229 which filters all of the signals in the near-field frequency range. For far-field wireless transmission, the damping coil 216 can be driven with signals 231 via the coupler 222 (e.g., both directivity and coupling are equivalent, meaning that the received signal will be attenuated as much as the emitted signal). Since the wireless circuitry will multiplex the receiving and transmitting stage, both signals 231 and signals 223 can pass through the coupler 222. Thus, connection 230 (with the coupler 222, capacitors 226(A) and/or 226(B), with coil 216) operate as the transmission antenna.

Figure 3:
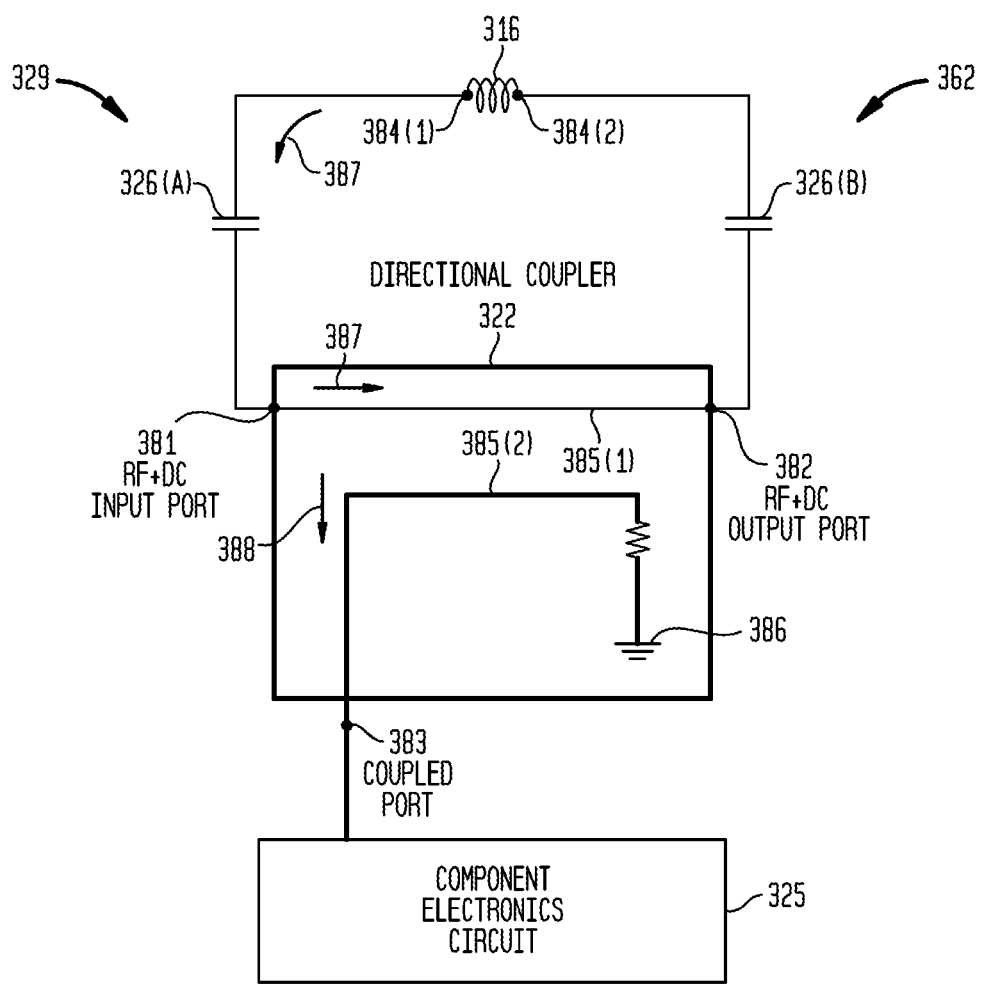
FIG. 3 is a simplified schematic diagram illustrating an isolation circuit, in accordance with certain embodiments presented herein.

As noted, isolation coupler 222, as well other isolation couplers in accordance with embodiments presented herein, may be implemented in a number of different manners. FIG. 3 is a schematic diagram illustrating one example arrangement for isolation coupler 222, in accordance with embodiments presented herein. In this embodiment, the isolation coupler 222 is a directional coupler and is referred to herein as directional coupler 322.

Directional coupler 322 comprises an input port 381, an output port 382, and a coupled port 383. The input port 381 is connected to the positive terminal 384(1) of a coil (loop antenna) 316 via capacitor 326(A), while output port 382 is connected to the negative terminal 384(2) of the coil 316 via capacitor 326(B). The capacitors 326(A) and 326(B), along with the inductance of the primary side of the coupler 372, form a high-pass filter 329 for signals received at the coil 316. The coil 316, capacitor 326(A), and capacitor 326(B) may be substantially similar to dampening 216, capacitor 226(A), and capacitor 226(B), respectively, described above with reference to FIG. 2. The coupled port 383 is connected to component electronics circuit 325, which may be substantially similar to component electronics circuit 225 of FIG. 2.

As shown, the directional coupler 322 also comprises two coupled transmission lines 385(1) and 385(2). Transmission line 385(1) is connected between input port 381 and output port 382, while transmission line 385(2) is connected between coupled port 383 and an internal load 386. In certain examples, transmission line 385(1) is referred to as a "mainline" or "primary side" of the coupler 322, while transmission line 385(2) is referred to as a "coupled line" or "secondary side" of the coupler 372. Each of the transmission lines 385(1) and 385(2) have an associated inductance and can be created using a number of different technologies, such as stripline technology, microstrip technology, etc.

The transmission lines 385(1) and 385(2) are physically separated from one another and, as such, provide direct current isolation there between. However, at least a segment of each of the transmission lines 385(1) and 385(2) are positioned sufficiently close together such that energy passing through transmission line 385(1) is coupled to transmission line 385(2). That is, due to the relative positioning of the two coupled transmission lines 385(1) and 385(2), a defined amount of the electromagnetic power in transmission line 385(1) passes to transmission line 385(2) and, accordingly, to the coupled port 383 and the component electronics circuit 325.

In FIG. 3, arrows 387 illustrate the flow of current from coil 316 through transmission line 385(1). Arrow 388 illustrates the coupled current that flows through transmission line 385(2) to coupled port 383. As shown, transmission line 385(1) closes the coil 316 while, due to the physical separation of the transmission lines 385(1) and 385(2), the component electronics circuit 325 is isolated (protected) from direct current at the coil 316.

Figure 4:
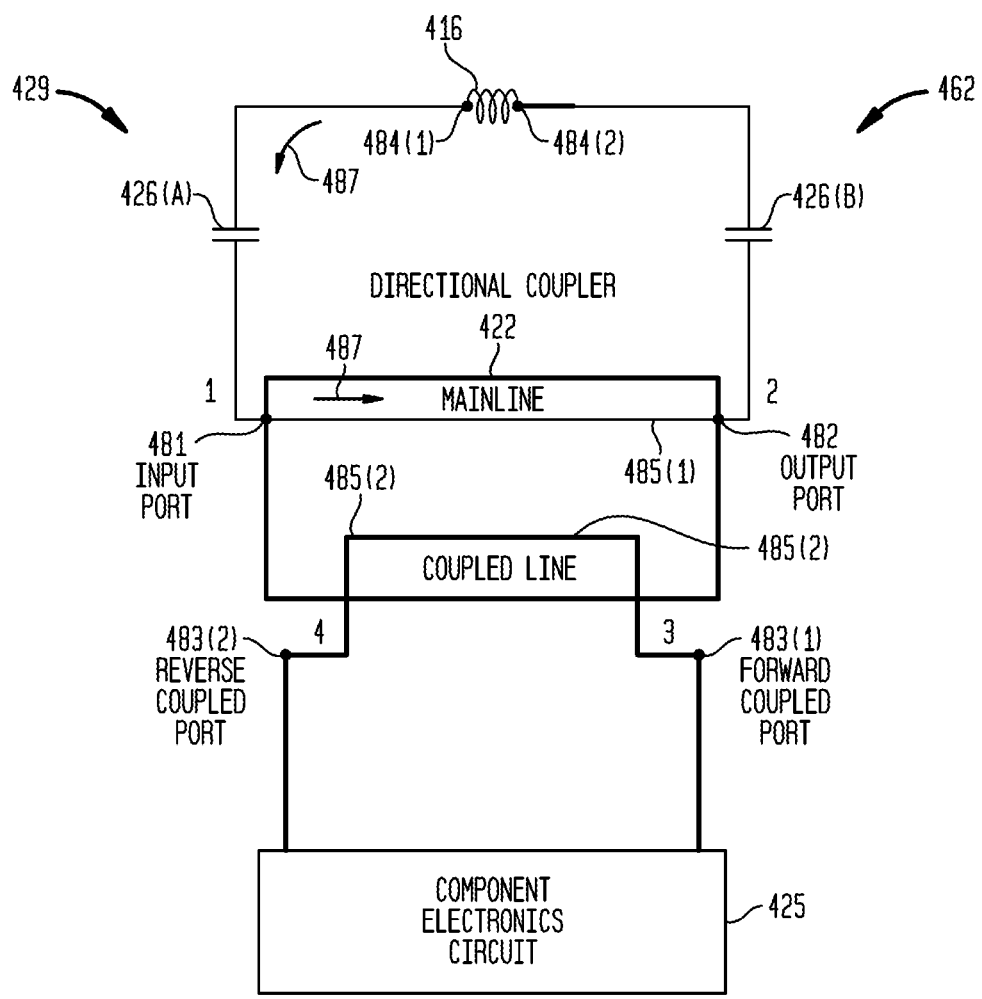
FIG. 4 is a simplified schematic diagram illustrating another isolation circuit, in accordance with certain embodiments presented herein.

FIG. 3 is an example of a three (3) port directional coupler. It is to be appreciated that the use of a three port directional coupler is illustrative and that other directional couplers may be used in other embodiments. For example, FIG. 4 is a schematic diagram illustrating a four (4) port directional coupler 422 that can be used in accordance with embodiments presented herein. The directional coupler 422 is similar to the coupler 322 of FIG. 3 except that that both ends of the coupled line are coupled ports.

More specifically, directional coupler 422 comprises an input port 481, an output port 482, and a first coupled port 483(1) and a second coupled port 483(2). The first coupled port 483(1) is sometimes referred to herein as a "forward coupled" port, while the second coupled port 483(2) is sometimes referred to herein as a "reverse coupled" or "isolated" port. The input port 481 is connected to the positive terminal 484(1) of a coil (loop antenna) 416 via capacitor 426(A), while output port 482 is connected to the negative terminal 484(2) of the coil 416 via capacitor 426(B). The capacitors 426(A) and 426(B), along with the inductance of the primary side of the coupler 422, form a high-pass filter 429 for signals received at the coil 416. The coil 416, capacitor 426(A), and capacitor 426(B) may be substantially similar to dampening coil 216, capacitor 226(A), and capacitor 226(B), respectively, described above with reference to FIG. 2. The coupled ports 483(1) and 483(2) are connected to component electronics circuit 425, which may be substantially similar to component electronics circuit 225 of FIG. 2. In certain examples, the reverse coupled port 483(2) may be terminated with an external load (not shown in FIG. 4)

As shown, the directional coupler 422 also comprises two coupled transmission lines 485(1) and 485(2) that form the primary and secondary sides, respectively, of the coupler 422. Transmission line 485(1) is connected between input port 481 and output port 482, while transmission line 485(2) is connected between coupled ports 483(1) and 483(2). Similar to the above embodiments, the transmission lines 485(1) and 485(2) can be created using a number of different technologies (e.g., stripline technology, microstrip technology, etc.).

The transmission lines 485(1) and 485(2) are physically separated from one another. However, at least a segment of each of the transmission lines 485(1) and 485(2) are positioned sufficiently close together such that energy passing through transmission line 485(1) is coupled to transmission line 485(2). That is, due to the relative positioning of the two coupled transmission lines 485(1) and 485(2), a defined amount of the electromagnetic power in transmission line 485(1) passes to transmission line 485(2) and, accordingly, to the forward coupled port 483(1) and the component electronics circuit 425.

In FIG. 4, arrows 487 illustrate the flow of current from coil 416 through transmission line 485(1). Arrow 488 illustrates the induced (coupled) current that flows through transmission line 485(2) to forward coupled port 483(1). As shown, transmission line 485(1) closes the coil 416 while, due to the physical separation of the transmission lines 485(1) and 485(2), the component electronics circuit 425 is isolated (protected) from direct current at the coil 416.

FIGS. 3 and 4 illustrate example arrangements for isolation couplers in accordance with embodiments presented herein. In the example arrangements of FIGS. 3 and 4, the coupling is via two transmission lines. In further embodiments, the transmission lines may be replaced by coils so as to form an air transformer (i.e., a transformer without a magnetic core). In certain embodiments, an isolation coupler may be implemented as a balun operating as an air transformer.

Figure 5:
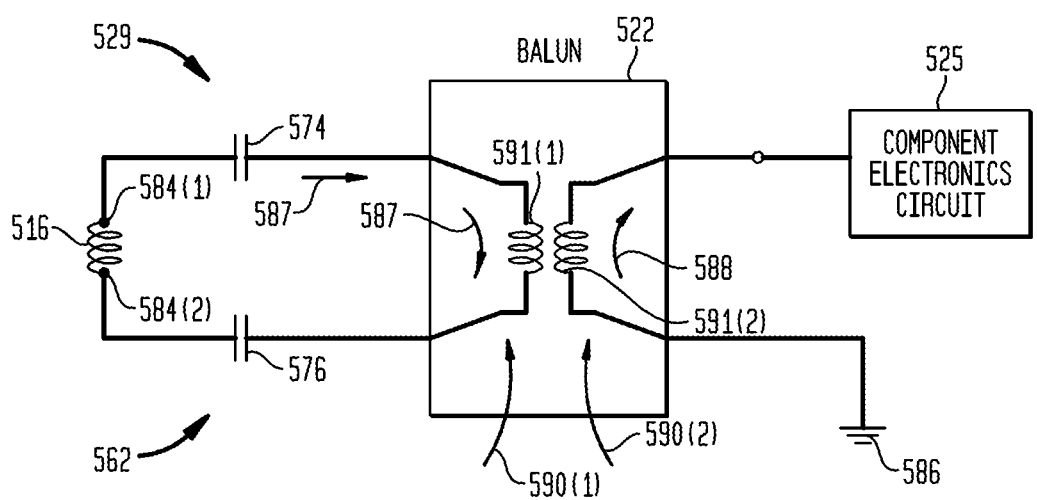
FIG. 5 is a simplified schematic diagram illustrating another isolation circuit, in accordance with certain embodiments presented herein.

For example, FIG. 5 is a simplified schematic diagram illustrating one arrangement in which the isolation coupler is formed by a balun 522. In this example, the balun 522 operates as an air transformer or directional coupler and comprises a primary side 590(1) and a secondary side 590(2). The primary and secondary sides 590(1) and 590(2) include coils 591(1) and 591(2), respectively.

The primary side 590(1) of the balun 522 is connected between positive terminal 584(1) of a coil (loop antenna) 516 via capacitor 526(A) and the negative terminal 584(2) of the coil 516 via capacitor 526(B). The capacitors 526(A) and 526(B), along with the inductance of the primary side of the coupler 522, form a high-pass filter 529 for signals received at the coil 516. The coil 516, capacitor 526(A), and capacitor 526(B) may be substantially similar to coil 216, capacitor 226(A), and capacitor 226(B), respectively, described above with reference to FIG. 2. The secondary side 590(2) of the balun 522 is connected between a load 586 and component electronics circuit 525, which may be substantially similar to component electronics circuit 225 of FIG. 2.

The coils 591(1) and 591(2) are physically separated from one another but are positioned sufficiently close together such that energy passing through coil 591(1) is coupled to coil 591(2) and, as such, a defined amount of the electromagnetic power in 591(1) passes to 591(2) and the component electronics circuit 525. In certain examples, some inductance and capacitance may be added in line with the coils 591(1) and 591(2) to balance the output. For ease of illustration, such additional inductance and capacitance have been omitted from FIG. 5.

In FIG. 5, arrows 587 illustrate the flow of current from coil 516 through coil 591(1). Arrow 588 illustrates the induced (coupled) current that flows through coil 591(2). As shown, coil 591(1) closes the coil (loop) 516 while, due to the physical separation of the coils 591(1) and 591(2)2), the component electronics circuit 525 are isolated (protected) from the coil 516. That is, balun 522 isolates the component electronics circuit 525 from direct current at the coil 516.

Figure 6:
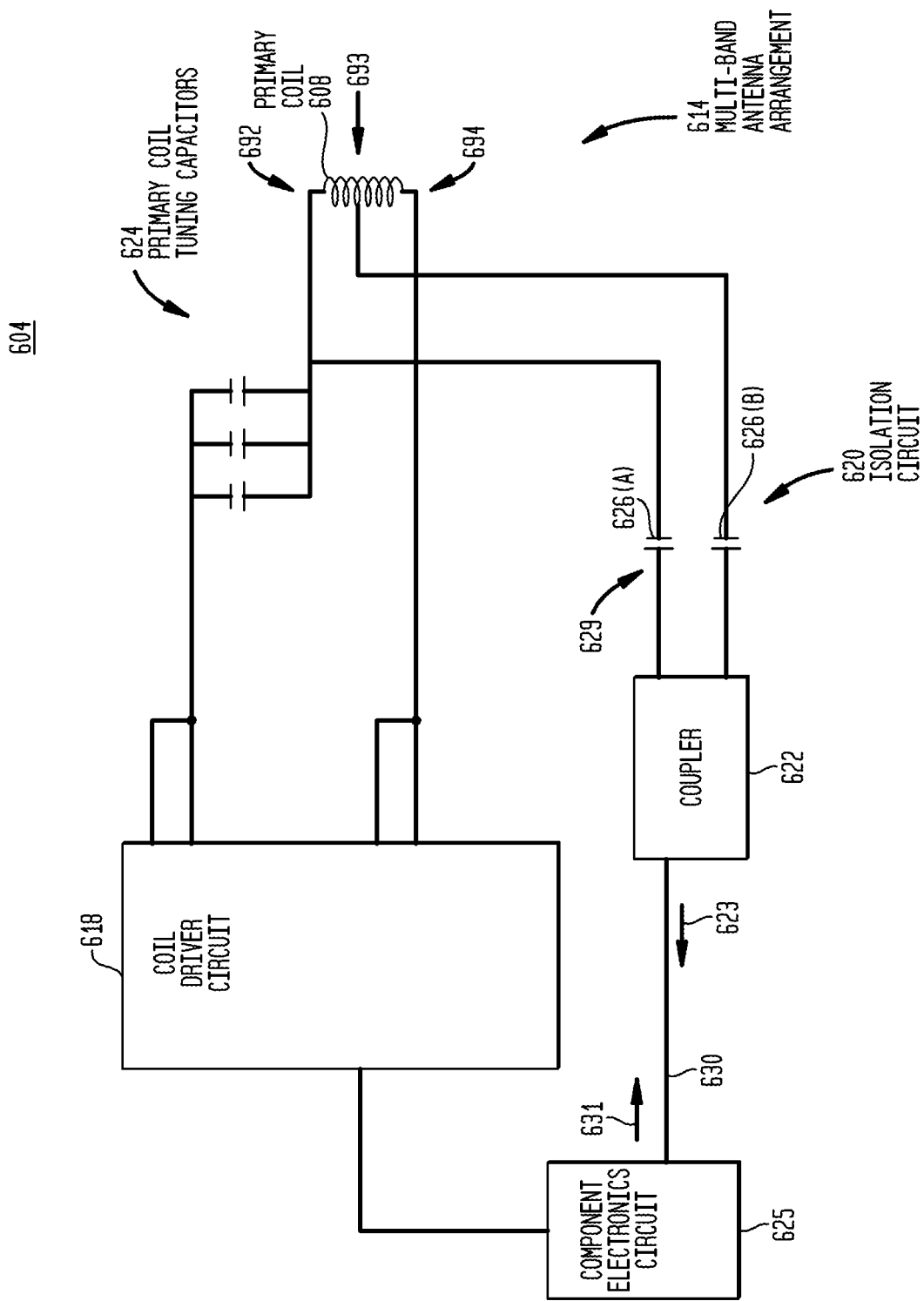
FIG. 6 is a simplified schematic diagram illustrating a medical device component, in accordance with certain embodiments presented herein.

As noted above, in the embodiment of FIG. 2, the multi-band antenna arrangement 214 includes a primary coil 208 and a dampening coil 216. It is to be appreciated that in alternative embodiments the multi-band antenna arrangement may include only a primary coil which is used for both near-field and far-field communication. For example, FIG. 6 is a simplified schematic diagram illustrating further details of another example external component, such as OTE component 104, that is configured in accordance with certain embodiments presented herein. For ease of description, the external component of FIG. 6 is referred to as external component 604.

External component 604 comprises a single transmitting/receiving antenna arrangement 614, sometimes referred to as a "multi-band antenna arrangement." In the example of FIG. 6, the multi-band antenna arrangement 614 comprises only a primary coil 608. The external component 604 also comprises, among other elements, a coil driver circuit 618, one or more primary coil tuning capacitors 624, and an isolation circuit 620. As shown, in FIG. 6 the isolation circuit 620 comprises an isolation coupler 622 and two capacitors 626(A) and 626(B), which form a high-pass filter with the coupler input. Each of the coil driver circuit 618 and the isolation coupler 622 have electrical connections to a component electronics circuit 625. The component electronics circuit 625 may comprise, among other elements, processors, memory, far-field wireless circuitry 627, etc. For ease of illustration, FIG. 6 only shows the far-field wireless circuitry 627 within the component electronics circuit 625.

In operation, the primary coil 608 is used for near-field communication with an implantable component (e.g., implantable component 102 of FIG. 1). That is, in order to transmit near-field signals to an implantable component, the coil driver circuit 618 drives the primary coil 608 with current signals which generate a modulated magnetic field which is measured by the implantable coil in the implantable component (i.e., via induced current flow in the implantable coil). When receiving near-field signals, the implantable coil within the implantable component similarly generates a modulated magnetic field, which induces a flow of current signals in the primary coil 608. The current signals received by (induced in) the primary coil 608 are provided to the coil driver circuit 618 and further processed for subsequent use by the external component 608.

As noted, in addition to near-field communication, external components in accordance with embodiments presented herein, such as external component 604, are also configured for far-field communication. In the embodiment of FIG. 6, the external component 604 also uses the multi-band antenna arrangement 614 (i.e., coil 608) for this far-field communication. That is, the same antenna arrangement 614 is used for both near-field communication with an implantable component and for far-field communication with other external devices.

In FIG. 6, the dual-use of the multi-band antenna arrangement 614 for both near-field and far-field communication is enabled by the isolation circuit 620. That is, the isolation circuit 620 is configured such that the multi-band antenna arrangement 614 may be used to transmit or receive both near-field signals and far-field signals, potentially at the same time.

As noted, the isolation circuit 620 comprises an isolation coupler 622 and two capacitors 626(A) and 626(B). In the example of FIG. 6, the isolation coupler 622 is connected to the primary coil 608 via the first capacitor 626(A) and the second capacitor 626(B) (i.e., capacitors 626(A) and 626(B) are connected between the isolation coupler 622 and the multi-band antenna arrangement 614). The capacitors 626(A) and 626(B) form a high-pass filter for signals received at the multi-band antenna arrangement 614.

In the example of FIG. 6, only a subset of the turns within primary coil 608 may be used when receiving far-field signals. That is, as shown in FIG. 6, the isolation circuit 620 may be connected between a first terminal 692 and an intermediate point 693 of the primary coil 608 (i.e., at point between the first terminal 692 and second terminal 694 of the coil). The intermediate point 693 is a point such that the number of turns between the first terminal 692 and the intermediate point 693 correspond to an advantageous wavelength for receipt of the far-field signals.

The isolation coupler 622 may be implemented in a number of different manners, such as in any of the manners described above with reference to FIG. 3, 4, or 5. However, in general, the isolation coupler 622 includes a first (primary) side (not shown in FIG. 6) that closes the antenna loop and a second (secondary) side (also not shown in FIG. 6) that is electrically isolated from the first side. The second side of the isolation coupler 622 generates a far-field output 623 that is provided to the component electronics circuit 625 via connection 630, while also electrically isolating the component electronics circuit 625, and far-field wireless circuitry 627, from direct current (DC) at the primary side connected to the multi-band antenna arrangement 614.

Due to the physical arrangement of the multi-band antenna arrangement 614, the coil 608 is exposed to both the near-field and far-field signals. However, in the embodiment of FIG. 6, the capacitors 626(A) and 626(B), and the inductance of the primary side of the coupler 622 operate as a high-pass filter 629 that blocks the higher-frequency near-field signals. In other words, the isolation circuit 620 operates to extract a portion of the signals present at multi-band antenna arrangement 614, without exposing the component electronics circuit 625, and particularly the far-field wireless circuitry 627, to damage resulting from the receipt of the near-field signals at the same antenna arrangement. In addition, local ground is not required at the first side of the isolation coupler 622.

In certain examples, some matching components may be potentially placed at connection 630 and/or near high-pass filter 629. For example, in one specific example, the matching component comprises a capacitor (e.g., a 2 pF capacitor)

in parallel with capacitors 626(A) and 626(B). In such examples, the matching component is used to convert the high-pass filter 629 to a specific (e.g., fifty (50) ohm) impedance. It is to be appreciated that this specific arrangement is merely illustrative and that other matching components may be provided in alternative embodiments.

In terms of transmission, the primary coil 608 can be driven directly at the near-field tuned frequency (as a result of the serial tuning capacitors 624). For far-field wireless transmission, the primary coil 608 can be driven with signals 631 via the coupler 622 (e.g., both directivity and coupling are equivalent, meaning that the received signal will be attenuated as much as the emitted signal). Since the wireless circuitry will multiplex the receiving and transmitting stage, both signals 631 and signals 623 can pass through the coupler 622. Thus, connection 630 (with the coupler 622, capacitors 626(A) and/or 626(B), with coil 608) operate as the transmission antenna.

Figure 7:
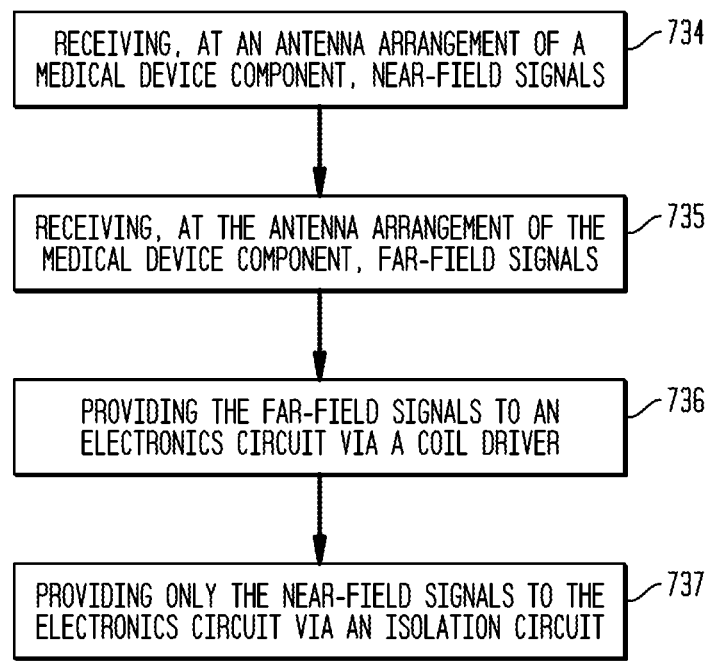
FIG. 7 is flowchart of a method, in accordance with certain embodiments presented herein.

FIG. 7 is a flowchart of a method 732 executed at a medical device component, in accordance with certain embodiments presented herein. Method 732 begins at 734 where an antenna arrangement of the medical device component receives near-field signals. At 735, the antenna arrangement of the medical device component received far-field signals. At 736, the far-field signals are provided to an electronics circuit via a coil driver, while at 737 only the near-field signals are provided to the electronics circuit via an isolation circuit.

Embodiments presented herein have primarily been described with reference to cochlear implant systems, in particular, have generally been described with reference to one example arrangement of a cochlear implant system configured to implement the techniques presented. However, as noted elsewhere wherein, the techniques presented herein may also or alternatively be used with other types of cochlear implant systems and/or any other implantable medical device system now known or later developed. Example systems in which the techniques presented may be implemented include, but are not limited to, other auditory prosthesis systems (e.g., systems that include auditory brainstem stimulators, electro-acoustic hearing prostheses, middle ear prostheses, bone conduction devices, direct cochlear stimulators, bimodal hearing prostheses, etc.) and/or other types of medical device systems, such as spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc. For example, FIG. 8 is a schematic diagram of one type of alternative medical device system, namely a pain relief system including a spinal cord stimulator, in which certain techniques presented herein may be implemented.

Figure 8:
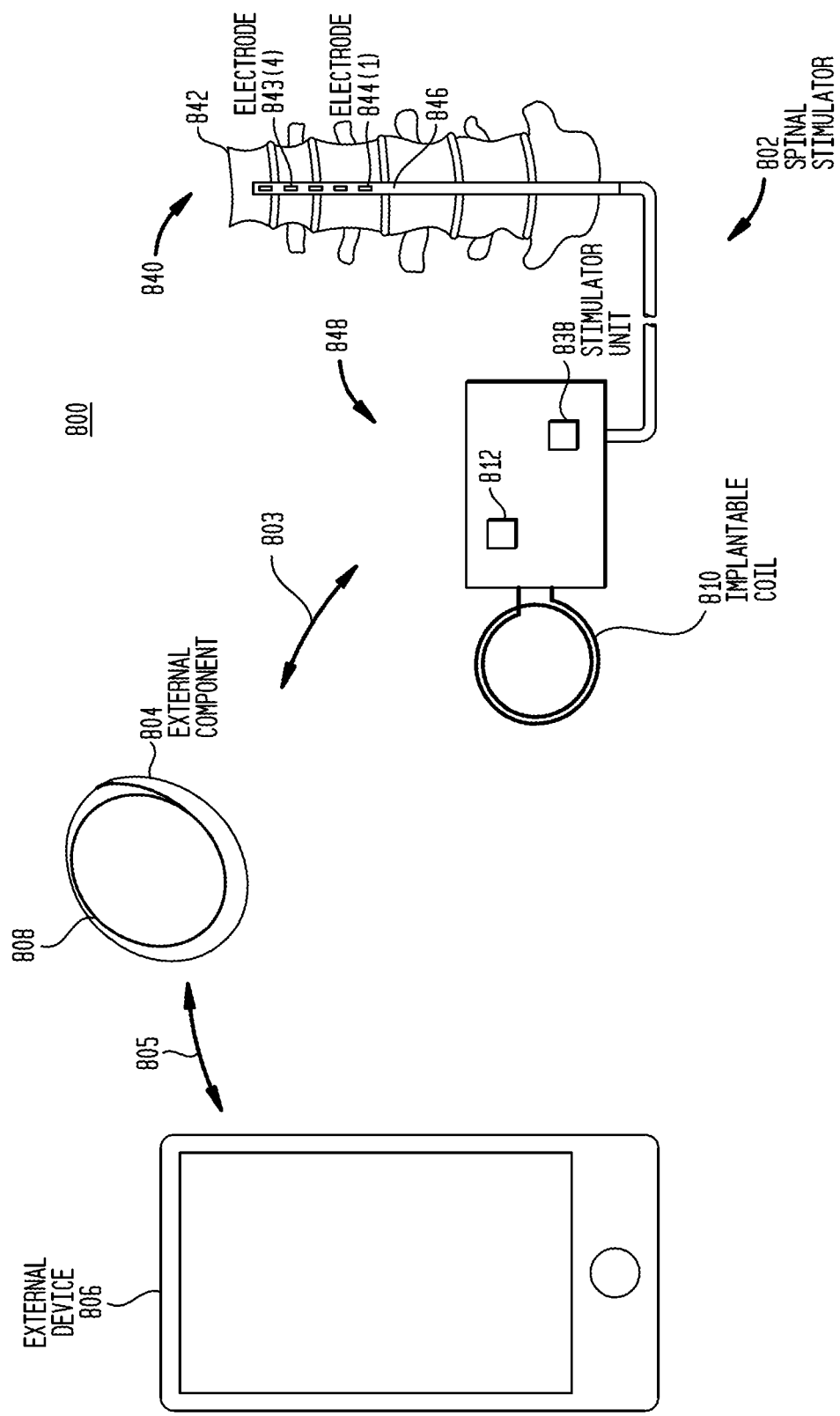
FIG. 8 is a schematic block diagram illustrating a spinal cord stimulator, in accordance with certain embodiments presented herein.
Figure 7:
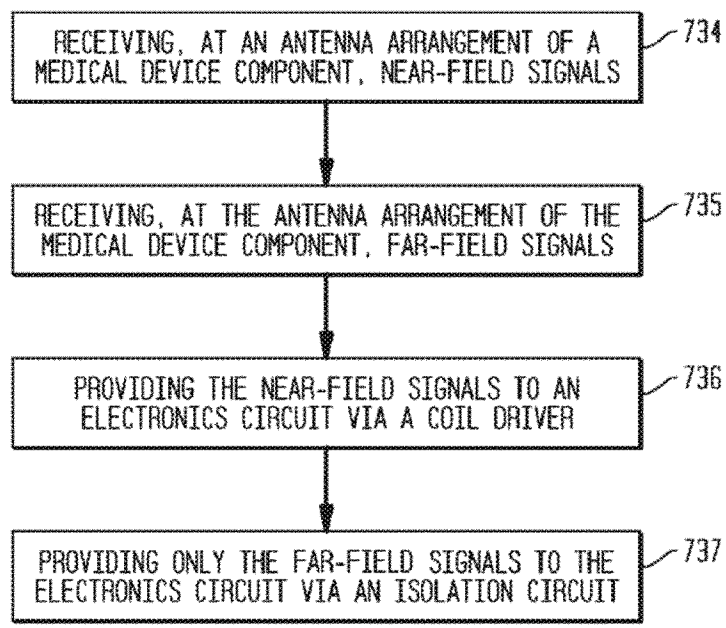

More specifically, the pain relief system 800 of FIG. 8 comprises an implantable component 802 configured to be implanted under the skin/tissue of a recipient, an external component 804, and an external device 806. The implantable component 802 is a spinal cord stimulator that comprises, among other elements, an implant body (main module) 848 and a stimulating assembly 840 implanted under the skin/tissue (tissue) of the recipient. The implant body 848 generally comprises, among other elements, an implantable coil 810, a magnet (not shown in FIG. 8) positioned proximate to the implantable coil assembly 810, a stimulator unit 838, and radio-frequency (RF) interface circuitry 812, which enables the spinal cord stimulator 802 to wirelessly communicate with external component 804.

The stimulating assembly 840 is implanted in a recipient adjacent/proximate to the recipient's spinal cord 842 and comprises five (5) stimulation electrodes 843, referred to as stimulation electrodes 843(1)-843(5). The stimulation electrodes 843(1)-843(5) are disposed in an electrically-insulating body 846 and are electrically connected to the stimulator unit 838 via conductors (not shown) that extend through the electrically-insulating body 846.

Following implantation, the stimulator unit 838 is configured to generate stimulation signals for delivery to the spinal cord 842 via stimulation electrodes 843(1)-843(5). In FIG. 8, external component 804 provides power and/or data to the spinal cord stimulator 802 for use in generating the stimulation signals and/or powering components of the spinal cord stimulator. It is to be appreciated that spinal cord stimulator 802 would include other components that, for ease of illustration, have been omitted from FIG. 8.

As shown in FIG. 8, the external component 804 is configured to wirelessly communicate with both the spinal cord stimulator 802 and the external device 806. That is, the external component 804 is configured for near-field wireless communication with the implantable component 802, and for far-field wireless communication with the external device 806. In FIG. 8, the near-field wireless communication between external component 804 and implantable component 802, sometimes referred to herein as a "near-field wireless link," is represented by arrow 803. Similarly, the far-field wireless communication between external component 804 and external device 806, sometimes referred to herein as a "far field wireless link," is represented by arrow 805. In general, the external component 804 may be implemented as described above with reference to FIGS. 2, 6, etc., so as to use a single transmitting/receiving arrangement for both the near-field and the far-field wireless communication. Shown in FIG. 8 is a primary inductive coil (primary coil) 808, which forms part of the transmitting/receiving arrangement used for both the near-field and the far-field communication. Other components of the transmitting/receiving arrangement have, for ease of illustration, been omitted from FIG. 8.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An external component of an implantable medical device system, comprising:
  a multi-band antenna arrangement;
  an electronics circuit;
  a coil driver coupled between the multi-band antenna arrangement and the electronics circuit and configured to at least one of send and receive, via the multi-band antenna arrangement, near-field signals from an implantable component inductively coupled to the multi-band antenna arrangement; and
  an isolation circuit coupled between the multi-band antenna arrangement and the electronics circuit and configured to at least one of send and receive, via the multi-band antenna arrangement, far-field signals from at least one external and to provide the far-field signals to the electronics circuit.

2. The external component of claim 1, wherein the isolation circuit is configured to electrically isolate the electronics circuit from direct current at the multi-band antenna arrangement.

3. The external component of claim 1, wherein isolation circuit comprises an isolation coupler and a high-pass filter connected between the isolation coupler and the multi-band antenna arrangement.

4. The external component of claim 3, wherein the isolation coupler is a directional coupler comprising:
a first transmission line having first and second ends connected to first and second terminals, respectively, of the multi-band antenna arrangement; and
a second transmission line physically separated from the first transmission line having at least a first end connected to the electronics circuit.

5. The external component of claim 4, further comprising:
a first capacitor connected between the first end of the first transmission line and the first terminal of the multi-band antenna arrangement; and
a second capacitor connected between the second end of the first transmission line and the second terminal of the multi-band antenna arrangement,
wherein an inductance of the first transmission line, the first capacitor, and the second capacitor collectively form the high-pass filter.

6. The external component of claim 5, further comprising:
at least one matching component connected between the first transmission line and the multi-band antenna arrangement.

7. The external component of claim 4, wherein a second end of the second transmission line is connected to an internal load.

8. The external component of claim 3, wherein the multi-band antenna arrangement comprises a primary coil and a dampening coil, and wherein the high-pass filter is connected between the isolation coupler and first and second terminals of the dampening coil.

9. The external component of claim 3, wherein the multi-band antenna arrangement comprises a primary coil and a dampening coil, and wherein the high-pass filter is connected between the isolation coupler and first and second terminals of the primary coil.

10. The external component of claim 3, wherein the multi-band antenna arrangement comprises a primary coil, and wherein the high-pass filter is connected between the isolation coupler and first and second terminals of the primary coil.

11. A medical device component, comprising:
an electronics circuit, including far-field wireless circuitry;
an antenna arrangement configured to receive near-field signals via an inductive coupling with a second medical device component and far-field signals from one or more external devices;
a coil driver disposed between the electronics circuit and the antenna arrangement and configured to provide the near-field signals to the electronics circuit;
an isolation coupler disposed between the electronics circuit and the antenna arrangement and configured to provide the far-field signals to the electronics circuit; and first and second capacitors connected in series with a primary side of the isolation coupler, and wherein the first and second capacitors are disposed on opposing sides of the primary side of the isolation coupler.

12. The medical device component of claim 11, wherein the isolation coupler comprises a directional coupler having a first transmission line and a second transmission line that is physically separated from the first transmission line.

13. The medical device component of claim 11, wherein the isolation coupler is configured to electrically isolate the electronics circuit from direct current at the antenna arrangement.

14. A method, comprising:
receiving, at an antenna arrangement of a medical device component, near-field signals via an inductive coupling with another medical device component;
receiving, at the antenna arrangement of the medical device component, far-field signals from an external device;
providing the far-field signals to an electronics circuit via a coil driver; and
providing only the near-field signals to the electronics circuit via an isolation circuit.

15. The method of claim 14, further comprising:
simultaneously receiving the near-field signals and the far-field signals at the antenna arrangement.

16. The method of claim 14, wherein providing only the near-field signals to the electronics circuit via an isolation circuit, comprises:
high-pass filtering signals received at the antenna arrangement to generate high-pass filtered signals; and
providing the high-pass filtered signals to an isolation coupler that is electrically connected to the electronics circuit.

17. The method of claim 16, wherein high-pass filtering signals received at the antenna arrangement, comprises:
filtering the signals received at the antenna arrangement with first and second capacitors connected in series with a primary side of the isolation coupler, and wherein the first and second capacitors are disposed on opposing sides of the primary side of the isolation coupler.

18. The method of claim 16, wherein the antenna arrangement comprises a primary inductive coil and a dampening inductive coil, wherein first and second capacitors are connected between the isolation coupler and first and second terminals, respectively, of the dampening inductive coil, and wherein high-pass filtering signals received at the antenna arrangement to generate high-pass filtered signals, comprises:
high-pass filtering signals received at the dampening inductive coil.

19. The method of claim 16, wherein the antenna arrangement comprises a primary inductive coil and a dampening inductive coil, and wherein first and second capacitors are connected between the isolation coupler and first and second terminals, respectively, of the primary inductive coil, and wherein high-pass filtering signals received at the antenna arrangement to generate high-pass filtered signals, comprises:
high-pass filtering signals received at the primary inductive coil.

20. The method of claim 16, wherein the antenna arrangement comprises a primary inductive coil, and wherein first and second capacitors are connected between the isolation coupler and first and second terminals, respectively, of the primary inductive coil, and wherein high-pass filtering signals received at the antenna arrangement to generate high-pass filtered signals, comprises:
  high-pass filtering signals received at the primary inductive coil.

* * * * *

UNITED STATES PATENT AND TRADEMARK OFFICE
CERTIFICATE OF CORRECTION

Page 1 of 2

PATENT NO. : 11,865,348 B2
APPLICATION NO. : 17/273170
DATED : January 9, 2024
INVENTOR(S) : Guilhem Yvan Vavelin et al.

It is certified that error appears in the above-identified patent and that said Letters Patent is hereby corrected as shown below:

In the Drawings

Please replace Fig. 7 with the Fig. 7 attached Replacement Sheet

In the Specification

Column 11, Line 25, please replace "the far-field signals are provided to" with --the near-field signals are provided to--

Column 11, Line 27, please replace "near-field signals are provided to" with --far-field signals are provided to--

In the Claims

Claim 14, Column 14, Line 20, please replace "providing the far-field signals" with --providing the near-field signals--

Claim 14, Column 14, Line 22, please replace "providing only the near-field signals" with --providing only the far-field signals--

Signed and Sealed this
Eighteenth Day of November, 2025

John A. Squires
*Director of the United States Patent and Trademark Office*